United States Patent [19]
Wiesner et al.

[11] 4,300,384
[45] Nov. 17, 1981

[54] METHOD AND APPARATUS FOR TAKING SAMPLES FOR THE DETERMINATION OF BREATH ALCOHOL CONTENT

[75] Inventors: Peter Wiesner, Ratekau; Ulrich Heim, Reinfeld, both of Fed. Rep. of Germany

[73] Assignee: Drägerwerk Aktiengesellschaft, Fed. Rep. of Germany

[21] Appl. No.: 119,421

[22] Filed: Feb. 7, 1980

[30] Foreign Application Priority Data

Feb. 22, 1979 [DE] Fed. Rep. of Germany ....... 2906908

[51] Int. Cl.³ ............................................. G01N 31/00
[52] U.S. Cl. ...................................... 73/23; 73/863.01
[58] Field of Search .................. 73/23, 27 R, 421.5 R; 128/719; 422/84

[56] References Cited

U.S. PATENT DOCUMENTS

| | | | |
|---|---|---|---|
| 3,854,320 | 12/1974 | Burroughs et al. | 73/23 |
| 3,858,434 | 1/1975 | Hoppesch et al. | 73/23 |
| 3,886,786 | 6/1975 | Hoppesch et al. | 73/27 R |
| 3,896,792 | 7/1975 | Vail et al. | 73/421.5 R |

*Primary Examiner*—Stephen A. Kreitman
*Attorney, Agent, or Firm*—McGlew and Tuttle

[57] ABSTRACT

A device and method for determining the alcohol content of a test person's breath comprising, a breathing sample line adapted to receive the test person's breath, a valve in the sample line for closing a flow of breath therein, a test chamber connected to the sample line downstream of the valve for receiving and testing the breath and a pressure sensing transducer connected to the sample line upstream of the valve for sensing the attainment of a predetermined pressure in the sample line. A clock is connected to the pressure sensing transducer and begins to operate when the preselected pressure has been obtained. The clock is connected to the valve and opens the valve only after the expiration of a preselected time period where the preselected pressure has been maintained throughout the period.

8 Claims, 1 Drawing Figure

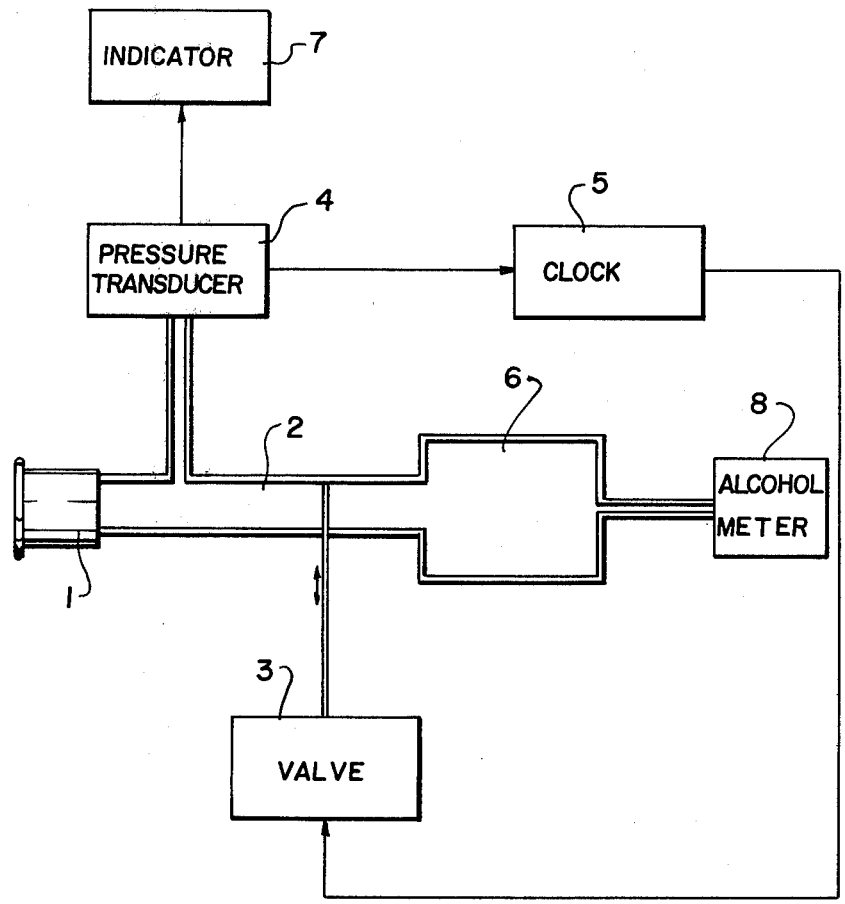

METHOD AND APPARATUS FOR TAKING SAMPLES FOR THE DETERMINATION OF BREATH ALCOHOL CONTENT

FIELD AND BACKGROUND OF THE INVENTION

The present invention relates in general to method and apparatus for determining the alcohol content of test person's breath and, in particular, to a new useful method and apparatus for determining such alcohol content by sampling a test person's breath only after it has been blown into a sample line and attained a preselected pressure for a preselected time period.

According to present understanding of the mechanism by which the alcohol of the body is transferred to the breathing air, a reliable breath alcohol test is only possible when a volume corresponding to the clearance or shuttle volume of the test person's breath which does not take part in gas exchange with and in the lungs, has already been exhaled and after a waiting period until the so-called "deep pulmonary air" (alveolar air) is present and the alcohol concentration has assumed a saturation value.

This concept is contradicted by more recent results which show that the breathing air is also equilibrated with the blood alcohol in the mucous membranes of the mouth, in the pharyingeal cavity and in the upper respirator tracts if it is given enough time. This air thus can be used for the determination of the blood alcohol content just like the deep pulmonary air is used.

The known measuring methods and arrangements for the determination of breath alcohol concentrations are based on the present concept.

A known arrangement for the determination of alcohol concentration, measures the alcohol in the breathing air at a time determined by a time control. This time is determined by the expiration of a given time interval starting within the exhalation period. The throughput of the breathing air must not drop, within this time interval below, a given minimum throughput, and must only flow in an exhaling direction. When these two conditions are not satisfied, an error detector determines the invalidity of the measurement. The given time interval ensures that the test person has already exhaled air from the oral cavity and from the trachea at the time of measurement, and that the measuring instrument then measures the alcohol concentration of the breathing air from the alveoli of the lungs. The expiration of the time interval is determined by the time at which a minimum breathing air volume of preferably at least 80% of the total breathing air volume has been exhaled. An integrator can integrate the breathing air during inhalation and exhalation and determine therefrom the expiration of the time interval after the minimum breathing air volume. This embodiment is to be independent of the physical structure of the test person. The method however, is not immune to measuring errors, caused by an uncooperative test person. By deliberate flat inhalation, the test person can simulate a low breathing capacity. The minimum breathing air volume, which is automatically established at 80% of the total breathing air volume, for example, can then originate practically only from the oral and pharyngeal cavity. The alveolar air, which is determined for an accurate measured value, is then not fully determined (DOS No. 24 28 352).

Another known method, and also the respective arrangement, solve this problem by means of an infrared measuring instrument which constantly measures the instantaneous alcohol concentration during the sampling.

A threshold comparator determines the variation of the measured values per unit of time, which is a measure for the rate of rise of the alcohol concentration.

A measured value is only transmitted when the rate of rise drops below a given threshold value. This first condition results from the fact that the portion of the shuttle air from the oral and pharyngeal cavity diminishes constantly with a dropping rate of rise, and that only alveolar air is in the measuring channel of the arrangement when it drops below the threshold value. Another condition for the transmission of the measured value is that the velocity of flow of the exhaled air determined by a flowmeter must have been above a given value during a given period before the measured value is transmitted. This additional condition ensures the provided course of the measuring method. The measurement of the alcohol concentration is effected by an infra-red measuring instrument with a short response time connected into the breathing air current. A disadvantage is that, because of the high resolution of the measured values, as is necessary for determining the rate of rise, an elaborate infra-red measuring instrument is required. A reliable determination of the alveolar air portion is not possible with a simple, inexpensive, but slow alcoholometers (DOS No. 26 10 578).

SUMMARY OF THE INVENTION

The object of the present invention is to provide a method and an apparatus which permits the taking of air samples equilibrated with the mucous membranes of the mouth and of the oral cavity, and of the upper respiratory tract, a mouth equilibrated sample for determining the breath alcohol content.

The advantages achieved with the invention consist particularly in that the taking and the determination of the mouth-equilibrated sample is extremely reliable, simple and also deception proof. It requires no elaborate flow and/or volume measurements. The sample is only introduced into the sample chamber after a sufficiently long period during which the breathing air can establish an equilibrium with the blood alcohol. The amount of breathing air is really taken only from the desired upper breathing area, both for big and for small test persons with respective large and small lung capacities. Interruption of the exhalation, possibly by deception, will close the sample chamber immediately. Fresh breathing air arriving in the oral cavity can only be exhaled into the sample chamber after the expiration of a given time interval in which the breathing air is in equilibrium again with the blood alcohol.

Complicated flow and volume measuring devices are not required. The few structural elements of the invention require no elaborate circuit arrangement. Known alcoholometers, even slow-measuring and simple devices, can be used for measuring the alcohol in the sample chamber.

According, an object of the present invention is to provide a device for determining alcohol content of a test person's breath comprising, a breath sample line adapted to receive a test person's breath, a valve in the sample line for closing a flow of breath therein, test chamber means connected to the sample line downstream of the valve for receiving and testing breath for its alcohol content, and pressure measuring and time determining means connected to the sample line upstream of the valve and to the valve for opening the valve only when a preselected pressure for a preselected time duration has been established in the sample line upstream of the valve.

A further object of the present invention is to provide a method for determining the alcohol content of a test person's breath comprising, having a test person blow into a sample line toward an alcohol test chamber, blocking the flow of breath in the sample line until a preselected pressure has been attained and maintained for a preselected period, and unblocking the flow of breath in the sample line to permit its flow into the test chamber after the preselected pressure for a preselected period has been maintained.

A still further object of the present invention to provide a device for determining the alcohol content of breath which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The only FIGURE of the drawing is a schematic block and diagrammatical view of one embodiment of the invention.

DESCRIPTION OF THE PREFERRED EMBODIMENT

Referring to the drawing in particular, the test person is asked to catch a breath and to blow into a mouthpiece 1. Sample line 2 adjoining mouthpiece 1, which leads to sample chamber 6 of an alcoholmeter 8 is closed by an electrically operated valve 3 at the start of the sampling. Consequently, a pressure builds up in sample line 2, which is determined by a pressure transducer 4. Pressure transducer 4 is designed as a threshold transmitter. When a given pressure threshold is exceeded e.g. 10 mbar, a following clock 5 is started. Clock 5 runs until the end of a given time interval, e.g. 10 seconds, and then causes the opening of valve 3 so that the exhaled air, which is now in equilibrium with any body alcohol, can flow into sample chamber 6. When the pressure in sample line 2 drops during this time interval below the pressure threshold, clock 5 is set back to zero and starts again only when the pressure threshold is exceeded again. This circuit ensures that after valve 3 is opened, only exhaled air can get into sample chamber 6 which is in equilibrium with the mucous membranes. In order to confine the amount of exhaled air to the oral and pharyingel cavity and the upper respiratory tract, clock 5 closes valve 3 again after a corresponding predetermined time interval.

After the breathing air sample has been received in sample chamber 6, it is analyzed there by the known alcoholometer 8.

Indicator 7 indicates to the test person the attainment of the pressure threshold and the end of the sampling.

While a specific embodiment of the invention has been shown and described in detail to illustrate the application of the principles of the invention, it will be understood that the invention may be embodied otherwise without departing from such principles.

What is claimed is:

1. A device for determining the alcohol content of a test person's breath by causing the breath to come into equilibrium with alcohol in the person's breathing tract before the breath is tested, comprising, a breath sample line adapted to receive the test person's breath, a valve in said sample line which has a closed position for stopping a flow of breath into the sample line, means defining a test chamber connected to said sample line downstream of said valve for receiving breath only when said valve is open, an alcohol sensor connected to said test chamber for testing breath in said chamber for its alcohol content, and pressure determining and time period means connected to said sample line upstream of said valve and to said valve, for opening said valve only when a predetermined pressure has been attained and maintained for a predetermined time period in said sample line upstream of said valve which is sufficient to establish equilibrium of alcohol in the breath of upstream of said valve and the person's breathing tract.

2. A device according to claim 1, wherein said valve comprises an electronic valve.

3. A device according to claim 1, wherein said pressure determining and time period means comprises a pressure transducer connected to said sample line upstream of said valve, a clock connected to said pressure transducer and to said valve for opening said valve after the expiration of the preselected time period, the preselected time period being started only after said preselected pressure has been established and maintained throughout the time period.

4. A device according to claim 3, including an indicator connected to said pressure transducer for indicating the attainment of the preselected pressure.

5. A device according to claim 3 wherein said clock is restarted to the beginning of the preselected time period if, once the preselected pressure has been attained, the pressure of breath in the sample line falls below the preselected pressure.

6. A method for determining the alcohol content of a test person's breath using breath from the person's upper breathing tract, comprising, having a test person blow into a sample line toward an alcohol test chamber, locking the flow of breath in the test line until a preselected pressure has been attained and maintained for a preselected time period so that an equilibrium is established for alcohol in the blocked breath and in the person's upper breathing tract, and unblocking the flow of breath in the sample line to permit a flow of breath which has alcohol in equilibrium with the alcohol in the person's upper breathing tract, into the alcohol test chamber to test its alcohol content only after the preselected pressure has been attained and maintained for the preselected time period.

7. A method according to claim 6 including indicating the attainment of the preselected pressure in the test line.

8. A method according to claim 6 comprising restarting the preselected time period when the pressure in the sample line, once attaining the preselected pressure, falls below the preselected pressure.

* * * * *